(12) United States Patent
Combs et al.

(10) Patent No.: US 10,569,208 B2
(45) Date of Patent: Feb. 25, 2020

(54) FILTER CUSTOMIZATION SYSTEMS AND METHODS

(71) Applicant: SPRIMO, INC., Santa Clara, CA (US)

(72) Inventors: Raymond Combs, San Jose, CA (US);
Chunxiao Han, Dublin, CA (US);
Daniel K. Harden, Palo Alto, CA (US)

(73) Assignee: SPRIMO, INC., Santa Clara, CA (US)

( * ) Notice: Subject to any disclaimer, the term of this patent is extended or adjusted under 35 U.S.C. 154(b) by 566 days.

(21) Appl. No.: 15/276,644

(22) Filed: Sep. 26, 2016

(65) Prior Publication Data

US 2017/0087499 A1 Mar. 30, 2017

Related U.S. Application Data

(60) Provisional application No. 62/233,270, filed on Sep. 25, 2015, provisional application No. 62/233,273, filed on Sep. 25, 2015.

(51) Int. Cl.

| B01D 46/42 | (2006.01) |
| B01D 46/52 | (2006.01) |
| B01D 46/00 | (2006.01) |
| B01D 46/44 | (2006.01) |
| B01D 46/46 | (2006.01) |
| B01D 46/24 | (2006.01) |
| B01D 46/10 | (2006.01) |
| G01N 33/00 | (2006.01) |

(52) U.S. Cl.
CPC ......... *B01D 46/42* (2013.01); *B01D 46/0001* (2013.01); *B01D 46/0027* (2013.01); *B01D 46/0028* (2013.01); *B01D 46/0036* (2013.01); *B01D 46/106* (2013.01); *B01D 46/2414* (2013.01); *B01D 46/442* (2013.01); *B01D 46/448* (2013.01); *B01D 46/46* (2013.01); *B01D 46/521* (2013.01); *G01N 33/0011* (2013.01); *B01D 2273/18* (2013.01); *B01D 2275/10* (2013.01)

(58) Field of Classification Search
CPC ............ B01D 2273/18; B01D 2275/10; B01D 46/0001; B01D 46/0027; B01D 46/0028; B01D 46/0036; B01D 46/106; B01D 46/2414; B01D 46/42; B01D 46/442; B01D 46/448; B01D 46/46; B01D 46/521; G01N 33/0011
See application file for complete search history.

(56) References Cited

U.S. PATENT DOCUMENTS

| 6,778,864 B1 | 8/2004 | Bugli et al. |
| 6,916,239 B2 | 7/2005 | Siddaramanna et al. |

(Continued)

FOREIGN PATENT DOCUMENTS

WO 2012018766 A2 2/2012

*Primary Examiner* — Christopher P Jones
(74) *Attorney, Agent, or Firm* — Fish IP Law, LLP (57) ABSTRACT

Systems and methods for customizing a removable filter in an air purifier. The removable filter may comprise multiple filter types, and the combination and characteristics of the filter types can be varied based on air-quality requirements. In some instances, the composition of a new filter can be determined based on data obtained from analysis of used filters. Additionally, filters can be personalized based on an individual user's health data, geographic location, and regional and local air-quality characteristics.

17 Claims, 10 Drawing Sheets

(56) References Cited

U.S. PATENT DOCUMENTS

| | | |
|---|---|---|
| 7,041,147 B2 | 5/2006 | Huehn et al. |
| 2002/0078830 A1 | 6/2002 | Chung et al. |
| 2011/0168463 A1* | 7/2011 | Perkins ............... B60H 3/0071 180/65.21 |
| 2014/0083292 A1 | 3/2014 | Weiden |
| 2015/0000518 A1 | 1/2015 | Sullivan |

\* cited by examiner

FILTER CUSTOMIZATION SYSTEMS AND METHODS

This application claims the benefit of priority to U.S. Provisional Application 62/233,270 filed Sep. 25, 2015, and U.S. Provisional Application 62/233,273 filed on Sep. 25, 2015, the contents of which are incorporated by reference in their entireties. Where a definition or use of a term in a reference that is incorporated by reference is inconsistent or contrary to the definition of that term provided herein, the definition of the term provided herein is deemed to be controlling.

FIELD OF THE INVENTION

The field of the invention is air purification systems.

BACKGROUND

The background description includes information that may be useful in understanding the present invention. It is not an admission that any of the information provided herein is prior art or relevant to the presently claimed invention, or that any publication specifically or implicitly referenced is prior art.

Air quality is a concern in many parts of the world. Pollution, dust, allergens, and air-borne pathogens significantly impact the health of millions of people on a daily basis. As a result, many people use air purifiers in an attempt to improve indoor air quality.

Air purifiers typically work by passing air through a filter inside the air purifier device. In conventional systems, the air purifier may take the form of a standalone mobile air purifier for a room or small area, or may take the form of a central system that circulates air to multiple rooms. For example, one typical system is found U.S. Pat. No. 7,041,147 to Huehn et al., which describes an air purifying device with a filter element.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In more advanced systems, the air purifier system may include a variety of sensors, such as pollution sensors to determine the level of pollutants in the air, or air speed sensors to aid in the adjustment of the fan speed in order to attempt a certain level of air cleanliness. For example, U.S. Pat. No. 6,916,239 to Siddaramanna and Chavala describes an air quality system for purifying a building with a number of sensors to determine the count of people in the building as a way to properly ventilate the building.

Conventional home and office air purifiers have traditionally emphasized local air sensing to determine fan behavior in standalone portable air purifier systems. However, there are many drawbacks of this method including; the inability to determine if the air within the entire room is actually getting cleaned, the inability to compare indoor air quality with outdoors, inability to determine if the local room air is any cleaner as compared to the rest of the home or building, etc.

Additionally, in conventional systems, air filters typically are situated within the structure of an air purifier in such a way that several steps are required to get access to or replace or exchange the air filters. This approach has multiple drawbacks. For example, the act of disassembling the air purifier and removing the dirty air filters may result in the end user being exposed to the pollutants, either directly onto hands or gloves or indirectly by generating small plumes of dust in the air which can be breathed or settled on the skin, thus exposing the person servicing the air filter to these pollutants.

Thus, there is a need for an improved air purification system.

SUMMARY OF THE INVENTION

One aspect of the present inventive subject matter is directed to a filter customization system for an air purifier. The filter customization system includes a filter connected to the air purifier, and a communication module, and a filter module. The communication module and the filter modules are communicatively connected to the air filter.

The communication module is connected to an external sensor. The configurable filter module retrieves data from the communication module, and is programmed to modify a filter characteristic based on data from the communication module.

In some embodiments, the filter customization system also includes a user preference module which communicates with the configurable filter module. A user can program the configurable filter module via the user preference module. In some embodiments, the filter customization system is also connected to a database which contains air quality data about the air purifier's geographic location. In some embodiments, the configurable module may report data from the sensor to the database.

In some embodiments, the sensor can be a thermocouple, a humidity sensor, a particle sensor, a motion sensor, a distance sensor, a fan-speed sensor, or an air density sensor, light sensors, radio frequency (RF) sensors, humidity sensors, temperature sensors, vibration sensors, particulate matter sensors, motion sensors, distance sensors, fan-speed sensors, air density sensors, tag communication device (antenna), air pollutant sensors, gas sensors, total volatile organic compound sensors, carbon dioxide sensor, sensors for specific type of gas, for example, formaldehyde or nitrogen dioxide, noise sensor or other commercially suitable sensors for detecting an environmental condition. It is also contemplated that in some embodiments, the filter customization system may have more than one sensor.

Another aspect of the inventive subject matter is directed to a filter customization system for an air purifier capable of generating a profile for a filter coupled with the air purifier. A sensor is disposed within the filter, and the sensor is configured to generate a filter profile. A communication system connected to the sensor relays the filter profile. In some embodiments, more than one sensor communicates with the communication system to generate a filter profile.

In some embodiments, the filter is removable and replaceable. In some embodiments, a filter creation module communicates with the communication system, and the filter creation module uses the filter profile to generate a second filter. In some embodiments, the air purifier includes a fan.

Another aspect of the inventive subject matter is directed to a method for customizing an air purifier. To start, a first filter of an air purifier is analyzed to create a first filter profile. Next, a second filter is created using the first filter profile.

In some embodiments, the step of analyzing the first filter includes detecting and identifying particles caught in the first filter. In some embodiments, the method includes creating a regional profile, which may include regional air quality data, user health data, weather data, regional news data, GPS data, or data from other purifiers or sensors. The creation of the second filter can be based on the first filter profile and the regional profile.

In some embodiments the filter is one or more of a HEPA filter, ULPA filter, a MERV filter, an activated carbon filter, a gas absorption filter, a photo catalysis filter, a UV filter, an antibacterial filter or ionization filter, or a combination of different filter types. In some embodiments, the second filter has a different composition than the first filter. In some embodiments, the step of analyzing the first filter includes removing the first filter from the air purifier. In some embodiments the first filter profile is reported to a database.

The primary embodiment of the inventive subject matter utilizes various forms of data collection, data aggregation from multiple sources, plus programmatic software analysis based on algorithms in order to customize an air filter or an entire air filtration system.

DETAILED DESCRIPTION

The following description includes information that may be useful in understanding the present invention. It is not an admission that any of the information provided herein is prior art or relevant to the presently claimed invention, or that any publication specifically or implicitly referenced is prior art.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Various objects, features, aspects and advantages of the inventive subject matter will become more apparent from the following detailed description of preferred embodiments, along with the accompanying drawing figures in which like numerals represent like components.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

It is contemplated that there may be many situations in which an air purifier filter may need to be customized. Thus, various systems, apparatus, and methods are provided for a filter customization system. The inventive subject matter relates to indoor air cleaning or air purification systems and the filtering of air, with the desired effect of creating a healthier breathing environment. As used herein, the terms "air cleaner" and "air purifier" are used interchangeably to indicate a device or system to remove pollutants, particulates, volatile organic compounds, gases, etc. from the air within a home or building.

Figures 1, 2:
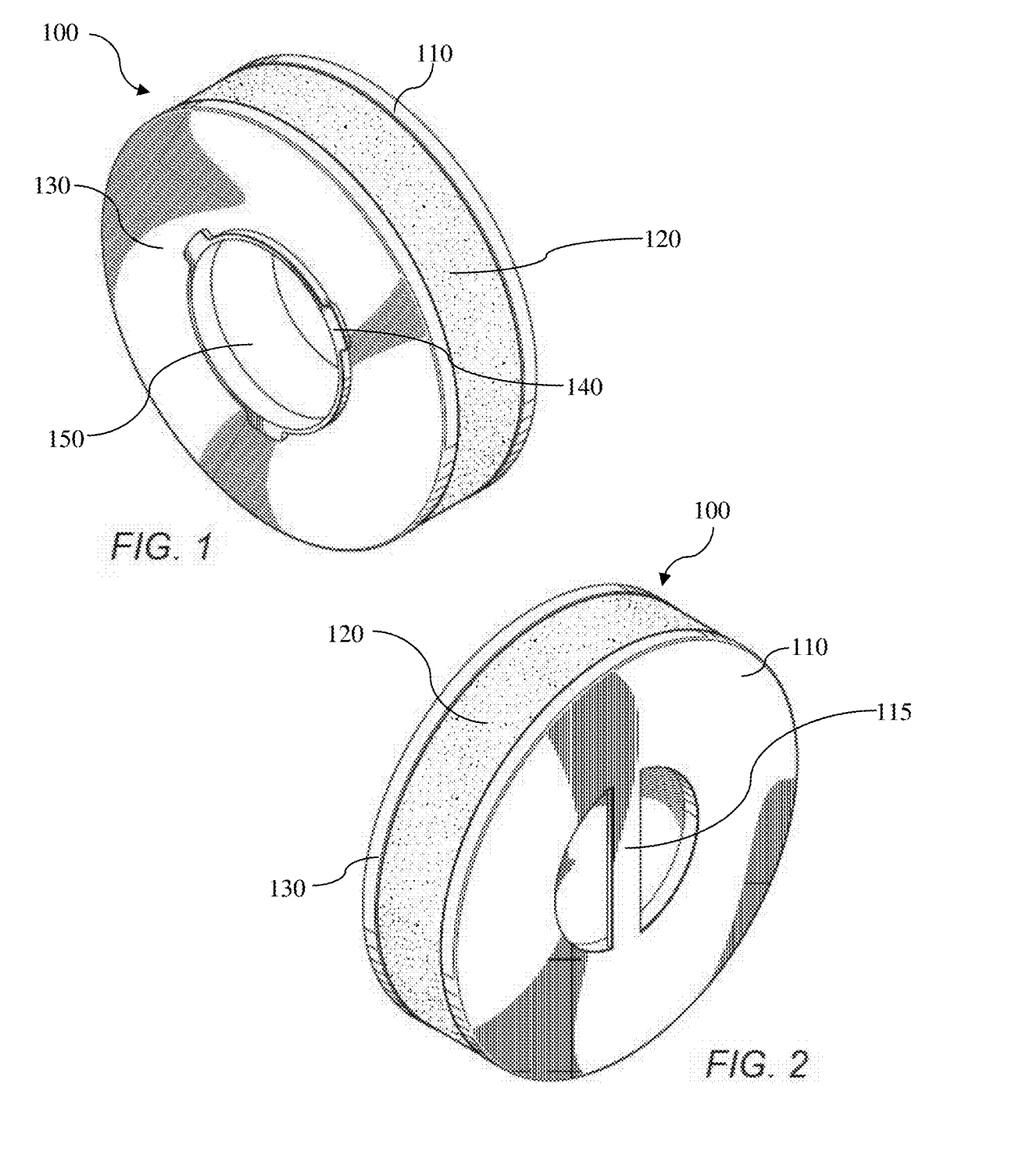
FIG. 1 illustrates a front-side perspective view of a customizable filter for an air purifier.
FIG. 2 illustrates a back-side perspective view of a customizable filter for an air purifier.

It is contemplated that one means for customizing an air filter provides for a removable air filter. FIG. 1 illustrates a removable air filter 100 for an air purifier. Air filter 100 has outer shell 110, filter matrix 120, inner shell 130, tooth 140, and hole 150.

FIG. 2 illustrates air filter 100 with outer shell 110, handle 115, filter matrix 120, and inner shell 130. In some embodiments, it is contemplated that air filter 100 is removable and/or replaceable from an air purifier. In some embodiments, tooth 140, or a plurality of teeth 140, interlock with the air purifier to secure air filter 100 in place. In some embodiments, a user or technician can remove air filter 100 from an air purifier by pulling on handle 115. In some embodiments, in order to remove air filter 100 from an air purifier (not shown), a user may twist and pull on 115 with one hand to release teeth 140 from engaging with the air purifier. To install a filter, the user would reverse the action by inserting the filter 100 at certain direction into the back of the purifier, then twists to the other direction to certain degree until a click sound. A haptic click sound indicates the male and female hubs are matched and thus filter is sealed tightly with the purifier. The one hand operation can greatly simplify the procedure of changing filter, saving time and also adding convenience to the process so that user may not be reluctant to change filter when it is needed.

It is contemplated that handle 115 can be designed differently to suit different sizes of hands or provide different ergonomic requirements. Other types of handle designs can be applied to fulfill certain requirements under different conditions, such as air purification, water purification or other applications.

Figure 3:
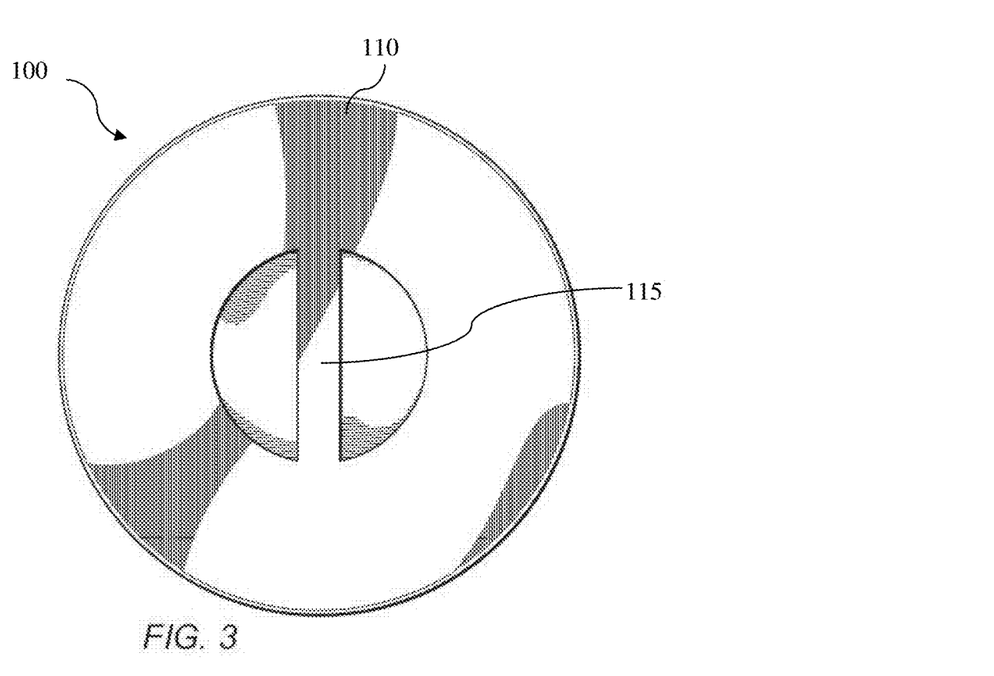
FIG. 3 illustrates a back-side view of a customizable filter for an air purifier.
Figure 4:
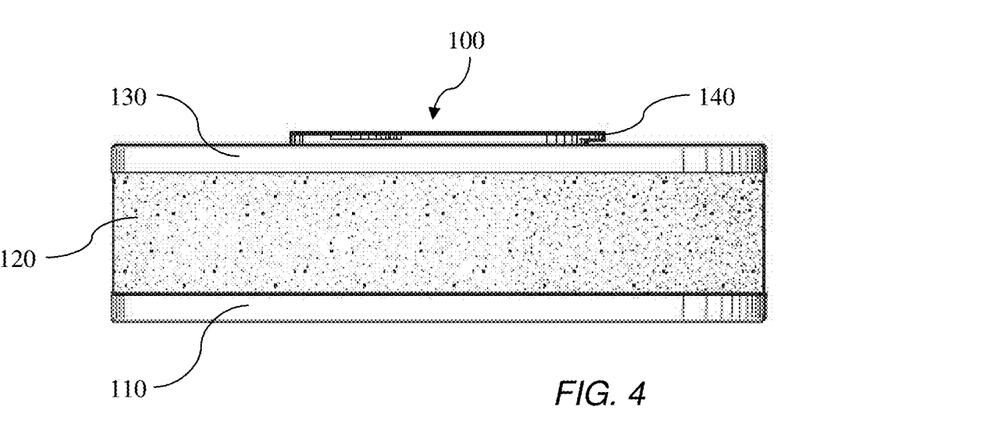
FIG. 4 illustrates a side view of a customizable filter for an air purifier.

FIG. 3 illustrates air filter 100 and shows outer shell 110 and handle 115. In FIG. 4, air filter 100 has outer shell 110, filter matrix 120, inner shell 130, and tooth 140.

Figure 5:
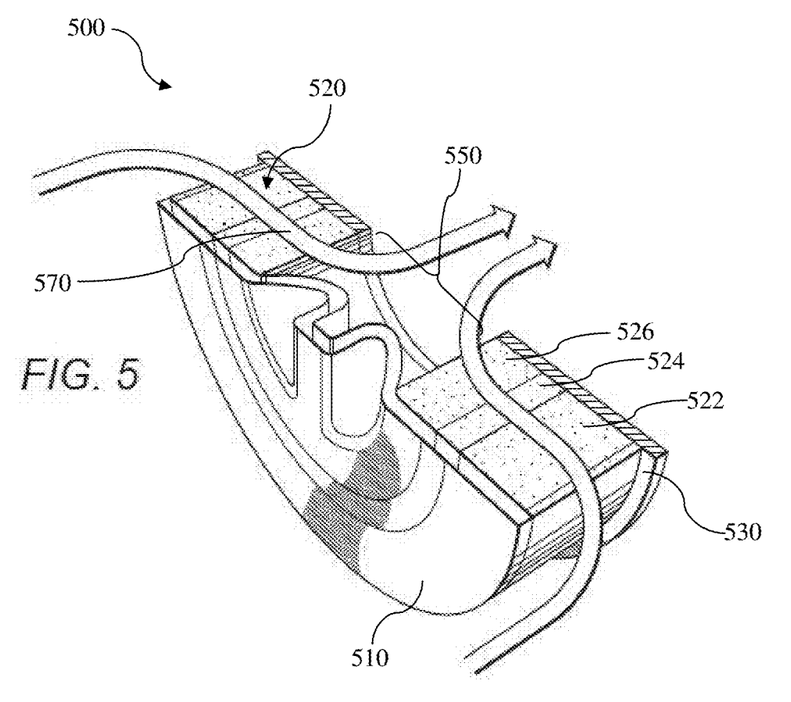
FIG. 5 illustrates a cross-sectional view of a customizable filter for an air purifier.

FIG. 5 illustrates a cross section of one contemplated embodiment of air filter 500. Air filter 500 has inner shell 530, outer shell 510, hole 550, and filter matrix 520, which has filter layers 522, 524, and 526. Air passes through the filter via air flow path 570. In some embodiments, air flow path 570 directs ambient air from the outside or wall of filter matrix 520 toward the center of hole 550.

It is contemplated that to simplify the filter replacement process filter matrix 520 can be composed of one or more different suitable filter types or materials. In other words, filter matrix 520 of some embodiments comprises multiple layers of filter elements, where each layer comprise a type of filter material for filtering out distinct pollutants. Additionally, each layer has a annular ring shape, such that the first layer is the most outer layer having the largest radius, the second layer has smaller radius than the first layer, and the last layer having the smallest radius and disposed in the inner most location of the filter matrix 520. In one example, filter matrix 520 can be composed of a pre-filter 522, an activated carbon filter 524, and a HEPA filter 526 integrated onto one single cartridge 500. Dirty air passes through the filter via air flow path 570, first through pre-filter 522, then through activated carbon filter 524, and finally through HEPA filter 526.

It is contemplated that different filter types or materials will have different effects on the air purification process. The materials capture, absorb, or treat the various pollutants and depending on the material, different pollutants can be captured by the air filter assembly or system. Different materials have different capacities to capture pollutants and may capture different types of pollutants at different efficiencies. For example, in some embodiments pre-filter 522 may capture 30%-100% of the particular matter (PM) in the range of 2-100 um in diameter. Activated carbon layer 524 may capture and volatile organic compounds (VOCs) such as formaldehyde, toluene, benzene and other gas phase compounds can be captured or reacted. HEPA filter 526 may capture smaller PM in the range of 0.01-10 um will be captured. It is contemplated that other embodiments may also include anti-bacterial layer to filter out biological contaminants such as fungi, virus or others. Any other suitable filter type (HEPA filter, activated carbon filter, UV filter, ionic filter, etc.) may be used alone or in combination with other filter types.

It is contemplated that when air goes through the whole filter media, pollutants such as PM and VOCs will be captured, retained or reacted, thus offering purified clean air to breathe. It is contemplated that the total number of filtering media layers can range from 2-50 in one single cartridge, depending on filtering function requirements. Additionally, the order and volume (depth) of the filtering media can also be arranged differently to meet certain purifying requirement.

Figure 6:
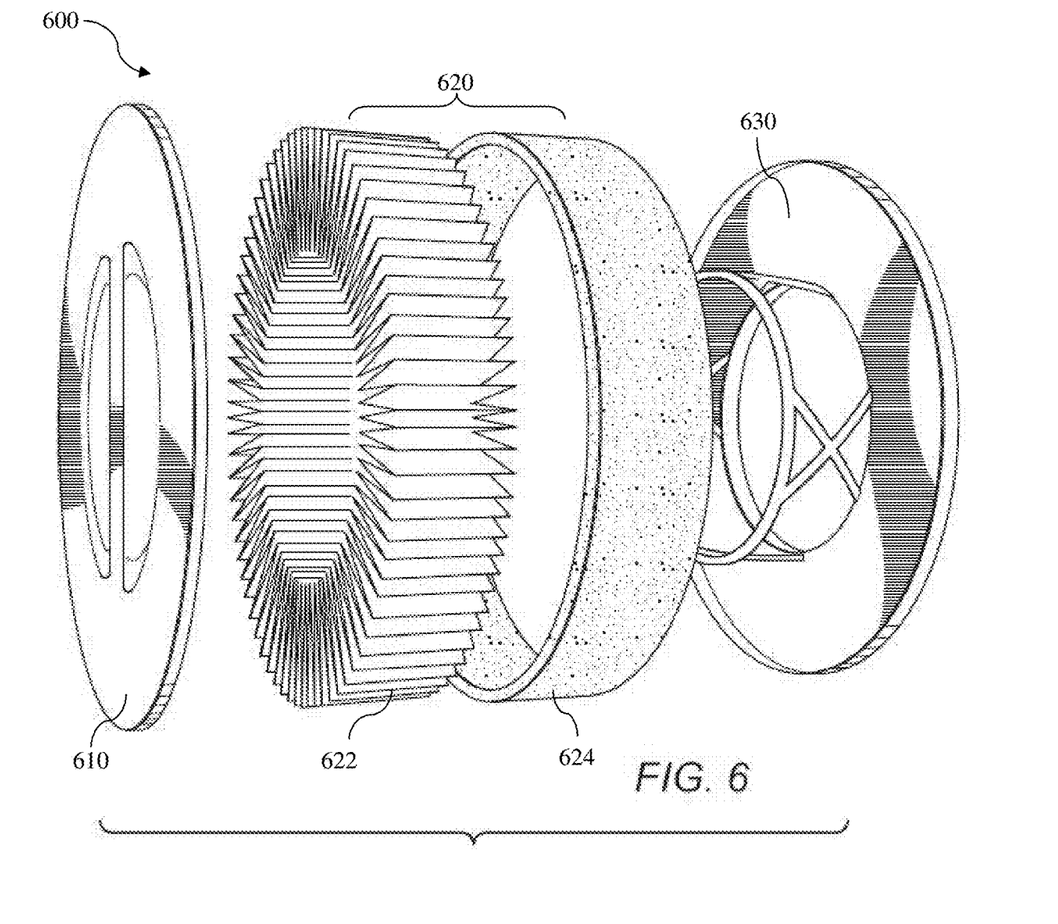
FIG. 6 illustrates an expanded view of one contemplated embodiment customizable filter for an air purifier.

FIG. 6 illustrates an expanded view of an alternate embodiment of an air filter 600. Air filter 600 has outer shell 610, filter matrix 620, with filter layers 622 and 624, and inner shell 630. In some contemplated embodiments a pre-filter 624 can be in the shape of an annular ring that surrounds the rest of the filter matrix 620, while a HEPA filter 622 and activated carbon filter (not shown) co-exist in pleated form. In some embodiments, activated carbon may be applied as a fine powder and sandwiched between two thin layers, thus enabling the folding and pleating of this material. It is contemplated that other suitable filtering materials, such as impregnated carbon or alumina, may also be applied to reach similar functionality.

Figure 7:
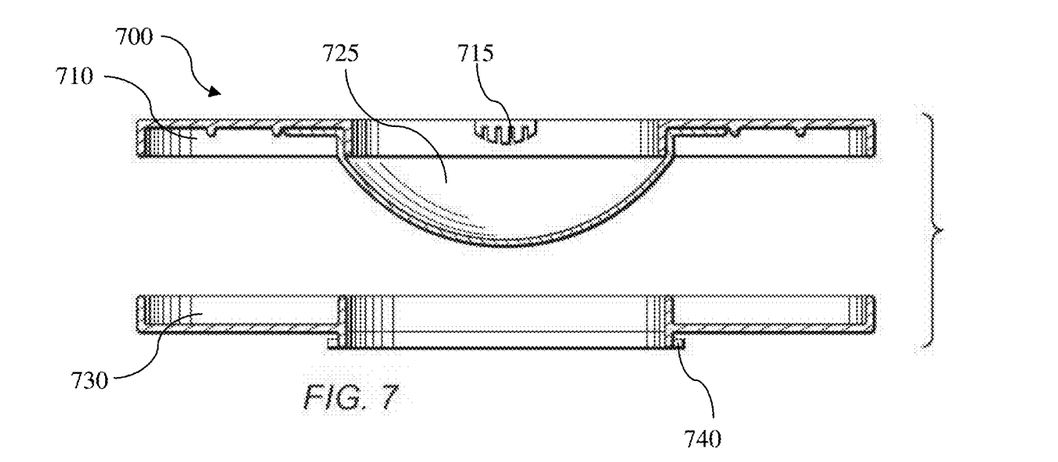
FIG. 7 illustrates a side cross-sectional view of one embodiment of a customizable filter for an air purifier.

FIG. 7 illustrates a shell 700 for an air filter. Shell 700 has outer shell 710 and inner shell 730. Outer shell 710 has handle 715 and depression 717. Inner shell 730 has tooth 740.

Figure 8:
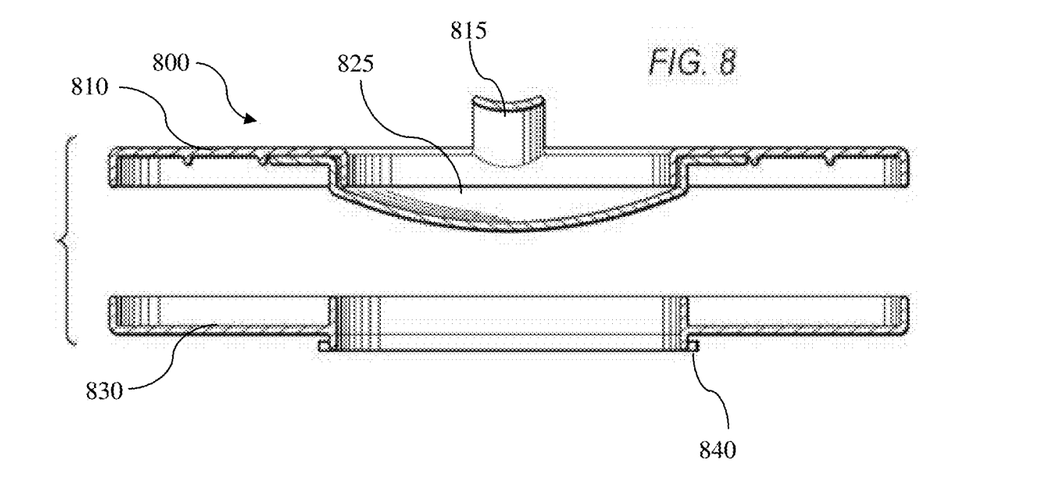
FIG. 8 illustrates a side cross-sectional view of one embodiment of a customizable filter for an air purifier.

FIG. 8 illustrates a shell 800 for an air filter. Shell 800 has outer shell 810 and inner shell 830. Outer shell 810 has handle 815 and depression 817. Inner shell 830 has tooth 840.

Figure 9:
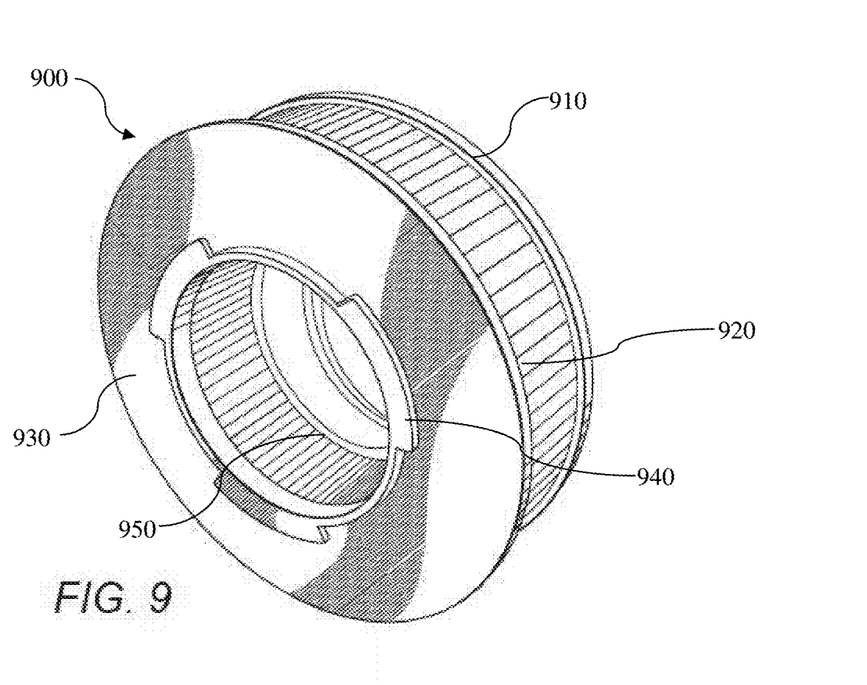
FIG. 9 illustrates a front-perspective view of an alternative embodiment of a customizable filter for an air purifier.

FIG. 9 illustrates an alternative embodiment for an air filter 900. Air filter 900 has outer shell 910, filter matrix 920, inner shell 930, tooth 940, and hole 950.

Figure 10:
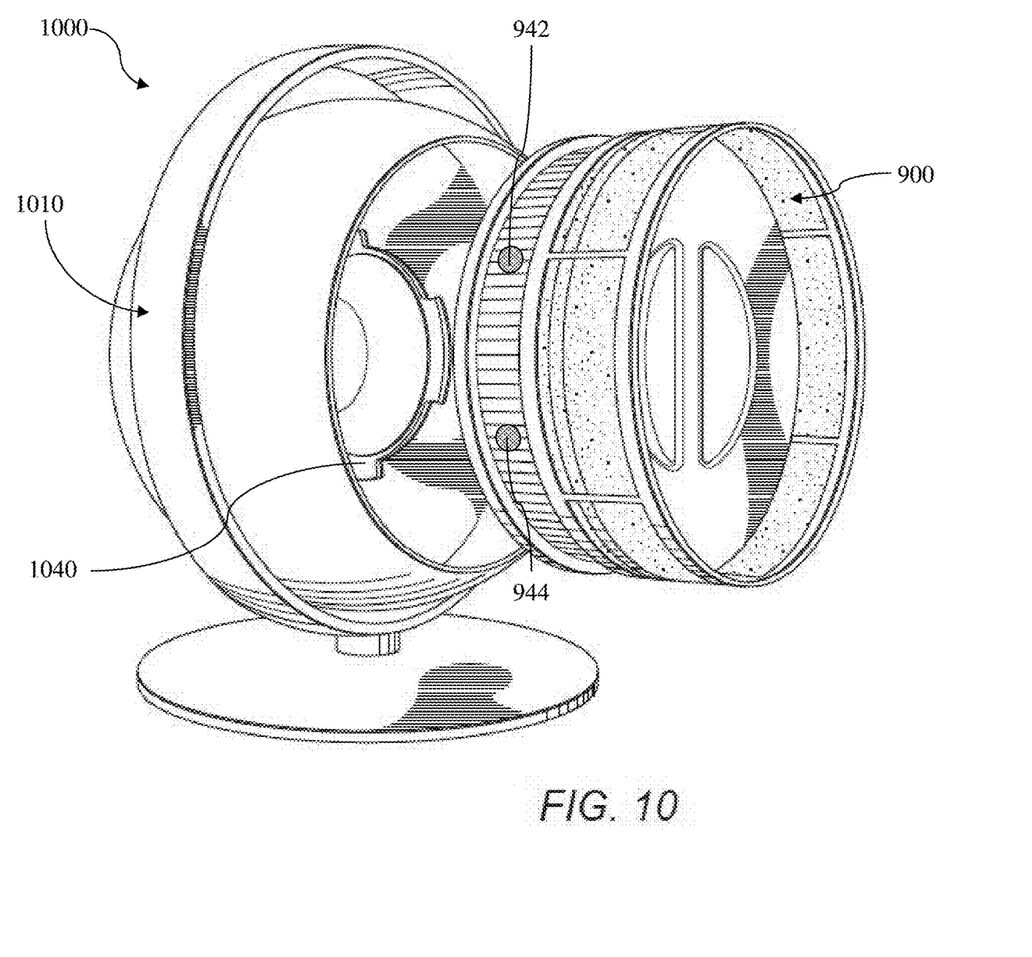
FIG. 10 illustrates an air purifier system with a removable filter.

FIG. 10 illustrates a portable air purifier 1100. Portable air purifier has a housing body 1010, with slot 1040, and air filter 900. Air filter 900 couples with housing body 1010 via a tooth (not pictured). Additionally, air filter 900 has sensors 942 and 944 coupled to the filter matrix. It is contemplated that air filter 900 can lock and seal to air purifier 100 via various mechanisms. In some embodiments, the sealing can be secured by an o-ring, a rubber seal, or other suitable method. It is preferred that minimal or zero air by-pass is allowed when the filter is sealed onto purifier. Details of the air purifier, including its structure and electronic components, can be found in the co-owned, co-pending application titled "Localized Ventilation Systems and Methods," which is incorporated by reference herein in its entirety.

In some embodiments, it is contemplated that air filter 900 can have one or more teeth 940, or male components, that are sized and dimensioned to mate with corresponding slots 1040, or female components, on housing body 1010, such that the teeth and slots may lock together and achieve an airtight seal. It is contemplated that the material of the teeth and slots could be rubber, plastic, or another material capable of creating an airtight seal.

In some embodiments, air filter 900 has one or more sensors 942 and 944 coupled to the filter and configured to sense a filter condition. Sensors 942 and 944 could be particulate matter sensors, thermocouples, humidity sensors, porosity sensors, UV sensors, humidity sensors, temperature sensors, vibration sensors, air density sensors, gas sensors, total volatile organic compound sensors, carbon dioxide sensor, sensors for specific type of gas, for example, formaldehyde or nitrogen dioxide, noise sensor, or other commercially suitable sensors for detecting an environmental condition. In some embodiments, sensor 942 and 944 can capture information about the age of the filter, the effectiveness of the filter, characteristic of filtered particles captured in the filter, etc. It is contemplated that in some embodiments sensors 942 and 944 can capture and relay information about the condition of filter 900 in real-time to a local or external database.

Figure 11:
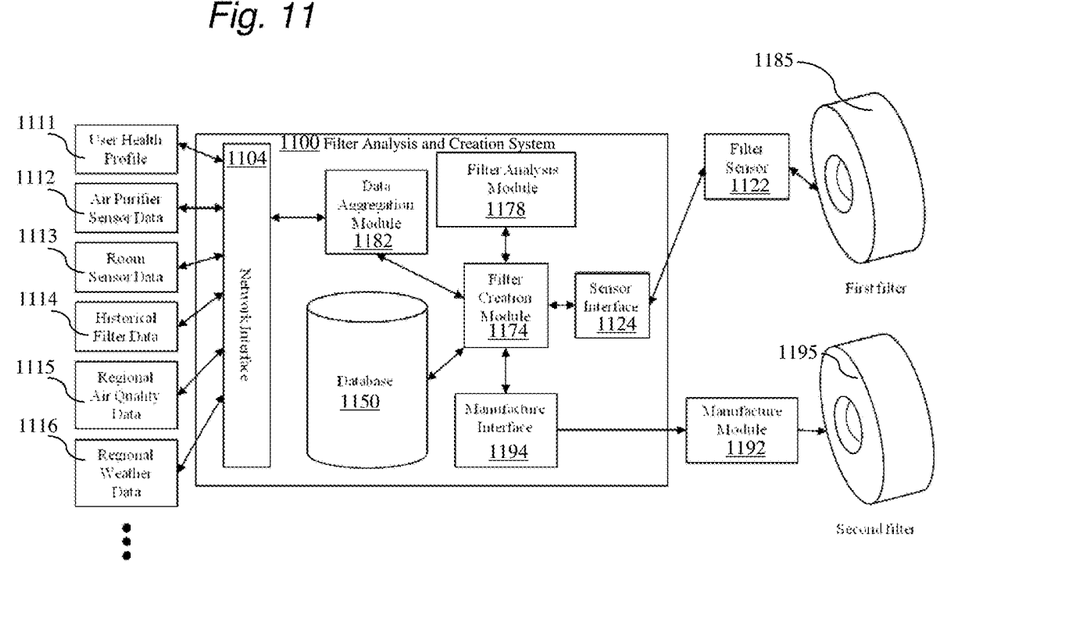
FIG. 11 illustrates a filter analysis and creation system.

FIG. 11 describes a filter analysis and creation system 1100 for analyzing a used, first filter 1185 and creating a new filter 1195. Filter analysis and creation system 1100 includes a filter creation module 1174. Filter creation module 1174 is programmed to communicate with one or more filter sensors 1122 for sensing a filter condition via a filter sensor interface 1124. Filter analysis and creation system 1100 also includes a filter analysis module 1178, a database 1150, a data aggregation module 1182, and a manufacture interface 1194. In some embodiments, the filter creation module 1174 interacts with a manufacture module 1192 via the manufacture interface 1194 to create a second, new filter 1195. In some embodiments, filter analysis and creation system 1100 can also be coupled, via network interface 1104, to a plurality of external data sources (e.g., user health profile source 1111, air purifier sensor data source 1112, room sensor data source 1113, historical filter data source 1114, regional air quality data source 1115, regional weather data source 1116, etc.), which each provide information about the local and regional environmental conditions, as well as the user's health, which can be used to inform the manufacture of the second filter 1195.

For example, user health profile data 1112 may contain personal demographic and health information about the end user of the personal air purifier, including age, gender, weight, health diagnoses, allergies, lung condition, heart rate, BMI, sleeping patterns, diet, etc. Such data may be useful in optimally tailoring a custom filter for the user.

In some contemplated embodiments, the air purifier system, in addition to filtering or purifying the air, is also programmed to sense the air quality and report to the central database the air quality and air characteristics within its immediate surroundings. In some embodiments, this can be accomplished by retrieving sensor data from an array of one or more sensors of various types embedded within the air purifier system. Some examples of sensors include sensors for temperature, humidity, volatile organic compounds (VOCs), gasses, particulate matter, oxygen content, carbon dioxide content, carbon monoxide content, radon, etc.

Air purifier sensor data 1112 includes historical, current, and forecasted data from sensors within the air purifier that relate to air purifier performance (e.g. fan speed), as well as ambient conditions in the air purifier's location, such as ambient air quality, temperature, humidity, light levels, etc. Similarly, room sensor data 1113 includes historical, current, and forecasted data from sensors located in the same room or building as the air purifier and may include data about ambient conditions in the room or building such as ambient air quality, temperature, humidity, light levels.

Historical air filter data 1114 includes data from past filters for a particular user, or particular region that may be used in generating a generating a filter profile and creating a custom filter for a particular user or location are also contemplated.

Regional air quality data 1115 is contemplated to include historical, current, and forecasted air quality data for the geographic region (e.g. neighborhood, city, county, state, country) surrounding the location of the air purifier, including particulate data, air quality data, pollution levels, allergen levels, etc. Regional air quality data 1115 may be obtained from a variety of sources, such as governmental reports, research stations, university, etc. as well as data from other air purifiers in the same region. Similarly, regional weather data 1116 is contemplated to include historical, current, and forecasted weather data (e.g. temperature, precipitation, humidity, barometric pressure) for the region surrounding the location air purifier, and similarly may come from any suitable source.

Other suitable data sources that may be useful in generating a filter profile and creating a custom filter for a particular user or location are also contemplated.

In some contemplated embodiments, filter analysis and creation system 1100 operates as follows. Filter analysis module 1178 is programmed to retrieve sensor data from a one or more filter sensors 1122 in order to analyze a filter condition of a first, used filter 1185. Sensor 1122 may be contained within filter 1185, or within an air purifier, or in the alternative may be externally located at a laboratory or analysis location. Thus, the first filter 1185 may be analyzed in situ in the air purifier, or it may alternatively be removed and analyzed at an external location.

In some embodiments, after the filter has been used and/or is expired, the entire filter assembly, or a piece of the filter media, or appropriate amount of the dust captured from the filter media can be shipped back to the lab for analysis. It is contemplated that overtime, dust that captured in the filter media will carry multiple layers of information in regards to the pollutant type and level in the living environment. For example, on the chemical level, the dust can be observed under microscope. Thus, by identifying types and amounts of pollutants, a general understanding of major pollutants can be obtained. It is contemplated that in some embodiments, different pollutants can be detected in this way, such as pollen, fibers, fungi/spores and skin cells.

It is further contemplated that on the biological level, by obtaining and extracting proteins from the captured dust, various biological assays can be performed including ELISA (enzyme-linked immunosorbent assay), PCR (Polymerase Chain Reaction), bacterial culture and other analytical biological tests. It is contemplated that analytical biological tests results might indicate biological contamination of the living space, including allergens and pathogens. For example, in some embodiments, an allergen report would have information such as dust mite allergen (Der f1 and Der p1), cat allergen (Fel d1), dog allergen (Can f1), cockroach allergen (Bla g1). In another example, in some embodiments, a pathogen report might indicate the types and levels of virus, bacterium, prion, fungus and all other microorganisms.

In some embodiments, filter analysis module 1178 is programmed to analyze sensor data retrieved from sensor 1122 by identifying any captured particles, allergens, pathogens, pollution, etc. captured in filter 1185. In some embodiments, in order for filter analysis module 1178 to analyze the first filter 1185, it is required to first dismantle or destruct filter 1185. In some contemplated embodiments, sensor(s) 1122 relay data collected to filter sensor interface 1124, which relays the information to filter creation module 1174 and filter analysis module 1178.

In some embodiments, sensor data can be combined with external data from external data sources 1111-1116 to determine characteristics required for the manufacture of a new filter. As such, filter analysis module 1178 of some embodiments is programmed to retrieve external data, such as user health data, air purifier data, user environmental data, historical filter data from external data sources (e.g., user health profile source 1111, air purifier sensor data source 1112, room sensor data source 1113, historical filter data source 1114, regional air quality data source 1115, regional weather data source 1116, etc.). Filter analysis module 1178 is programmed to generate a second filter profile by adjusting the first filter profile based on analysis of the external data Filter analysis module 1178 is then programmed to relay information about the second filter profile to the filter creation module 1174. Filter creation module is programmed to instruct the manufacture module 1192, via the manufacture interface 1194, to manufacture the second filter 1195 according to the second filter profile.

Figure 12:
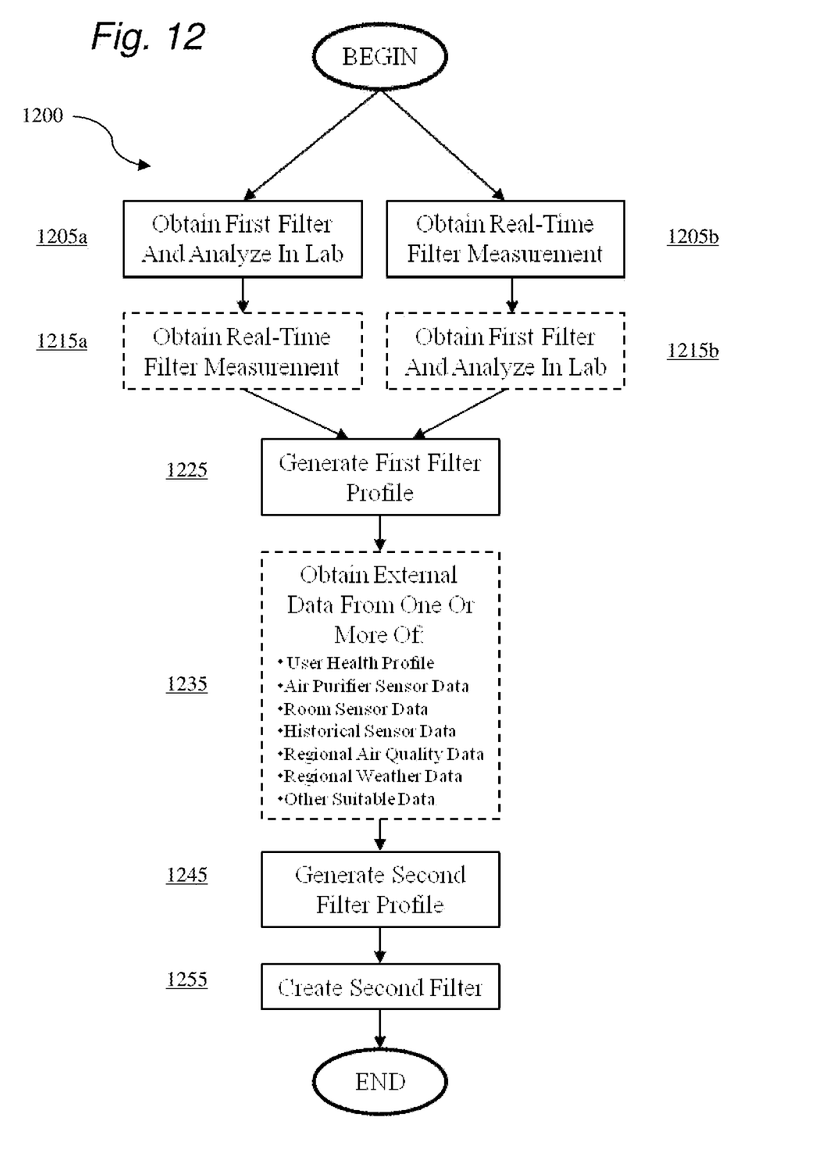
FIG. 12 illustrates a process for creating a filter of some embodiments.

The following example illustrates how one embodiment filter analysis and creation system 1100 would work: First, the system sends a user a notification that it is time to change their air filter in their portable air purifier. The dirty filter is analyzed and the captured particles are profiled and analyzed. The system determines there are high levels of NOx pollutants in the dirty air filter. The user's health data also indicates that the user is prone to pollen allergies, and the regional air quality forecast report indicates that the user's region will experience higher pollen levels than usual in the upcoming months. The filter analysis system might determine that a creation of a new filter with NOx filtering capability plus capability of filtering pollen would best benefit the user FIG. 12 illustrates a process 1200 for creating a new filter. The process 1200 begins with one of two options. The process may begin by either obtaining a first filter and analyzing in a lab (at step 1205a), and optionally obtaining a real-time filter measurement about a condition of the first filter (at step 1215a). In the alternative, the process may begin by obtaining a real-time filter measurement (1205b), and optionally obtaining the first filter an analyze in a lab (1215b). The process 1200 then uses (at step 1225) the analysis of the first filter and/or the analysis of real-time filter data to create a first filter profile. Next, in an optional step, (step 1235), the process 1200 obtains external data from one or more sources, such as user health profile data, air purifier sensor data, room sensor data, historical sensor data, regional air quality data, regional weather data, or other suitable data. The process 1200 then uses (at step 1245) data from prior steps to generate a second filter profile. Finally, the process (at step 1255) creates a second filter based on the second filter profile.

It is contemplated that the recommendations based on the first filter profile could be used to vary the composition of the second filter and also the construction of the second filter. There are multiple common techniques for varying the thicknesses or volumes of each layer, such as varying the pleated (folded) height of the individual materials, varying the number of pleats (folds) per inch/centimeter, or compressing the individual materials, among others. The varying thicknesses or volumes of each layer (A and B) can be set at manufacturing time as a permanent ratio, or the thicknesses can be varies in the field either by the end user or by a trained technician. Likewise, the exact materials used in each layer can be varied at manufacturing time for a more permanent ratio, or the materials may be exchanged or modified in the field by the end user or by a trained technician. Certain antibacterial chemicals can be also applied onto the existing filter media to offer antibacterial properties. The type of chemicals applied would be determined by the results of the filter chemical/biological analysis in the lab.

Figure 13A:
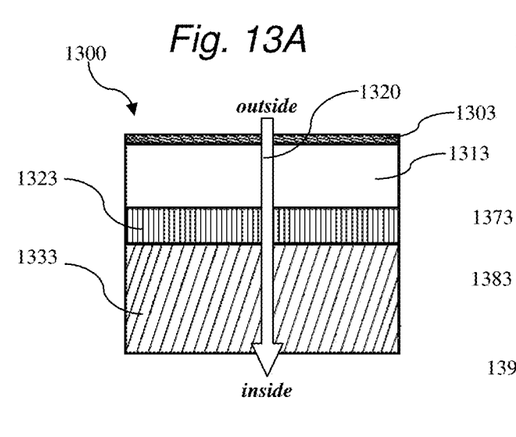
FIG. 13A and FIG. 13B illustrate cross-sections of two different example customized air filters based on generated air filter profiles.
Figure 13B:
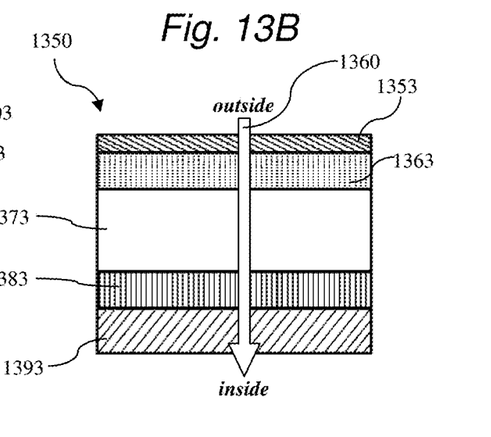

FIGS. 13A and 13B illustrate cross-sections of two example configurations of a customized air filter matrix that are manufactured based on two different filter profiles generated by the filter analysis and creation system 1100. In FIG. 13A, air filter matrix 1300 comprises layers 1303, 1313, 1323, and 1333. Air flow path 1320 flows first from the outside of air filter matrix 1300 through layer 1303, on through until it exits out of layer 1333. It is contemplated that based on the filter profile generated, layers can vary in number, composition, thickness, density, and filter type, according to the filter profile and customized for a particular user or location. The filter profile may be altered to target particular particles, pollutants, pathogens, chemicals, or allergens. FIG. 13B illustrates an alternative configuration of air filter matrix 1350, which has layers 1353, 1363, 1373, 1382, 1393. Airflow path 1360 flows first from the outside of air filter matrix 1350 through layer 1353, on through until it exits out of layer 1393.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A filter customization system comprising:
    an air purifier having a removable filter, wherein the removable filter comprises a first filter matrix;
    a sensor for determining a condition of the filter;
    one or more external data sources for determining a characteristic of a second filter matrix;
    a filter analysis module communicatively coupled with the sensor and the one or more external data sources;
    a filter creation module communicatively coupled with the filter analysis module;
    a database communicatively coupled to the filter analysis module and the filter creation module and configured to store data from the sensor and the one or more external data sources;
    a manufacture interface communicatively coupled with the filter creation module and configured to manufacture the second filter matrix according to a second filter profile;
    wherein the filter analysis module is programmed to (i) determine a first filter profile for the first filter matrix using data from the sensor and (ii) generate the second filter profile by adjusting the first filter profile based on an analysis of data from the one or more external data sources.

2. The filter customization system of claim 1, wherein the sensor is one of: a thermocouple, a humidity sensor; a particle sensor; a motion sensor; a distance sensor; a fan-speed sensor; an air density sensor.

3. The filter customization system of claim 1, further comprising a second sensor communicatively coupled to the filter analysis module.

4. The filter customization system of claim 1, further comprising a data aggregation module communicatively coupled with the filter analysis module and configured to aggregate data from the one or more external data sources.

5. The filter customization system of claim 1, wherein the database is communicatively coupled with the filter analysis module via an internet connection.

6. The filter customization system of claim 1, wherein the filter analysis module is coupled with the one or more external data sources via a network interface.

7. The filter customization system of claim 1, wherein the one or more external data sources comprises at least one of: a user health profile source, an air purifier sensor data source, a room sensor date source, a historical filter data source, a regional air quality data source, and a regional weather data source.

8. The filter customization system of claim 7, wherein the user health profile source comprises personal demographic and health information about an end user of the air purifier, including at least one of age, gender, weight, health diagnoses, allergies, lung condition, heart rate, BMI, sleeping patterns, and diet.

9. The filter customization system of claim 7, wherein the air purifier sensor data source comprises at least one of (i) air purifier performance data, including fan speed, and (ii) an ambient condition, including ambient air quality, temperature, humidity, and light levels.

10. The filter customization system of claim 7, wherein the room sensor date source comprises ambient conditions in the room or building where the air purifier is located, including ambient air quality, temperature, humidity, and light levels.

11. The filter customization system of claim 7, wherein the historical filter data source comprises data from past filters for a particular user or particular region.

12. The filter customization system of claim 7, wherein the regional air quality data source comprises air quality data for a geographic region surrounding a location of the air purifier, and includes at least one of particulate data, air quality data, pollution levels, and allergen levels.

13. The filter customization system of claim 7, wherein regional weather data source comprises weather data for a region surrounding a location of the air purifier, and includes at least one of temperature, precipitation, humidity, and barometric pressure.

14. The filter customization system of claim 1, wherein the removable filter comprises the first filter matrix removably disposed between an inner shell and an outer shell.

15. The filter customization system of claim 1, wherein the sensor is contained within at least one of the filter and the air purifier.

16. The filter customization system of claim 1, wherein the sensor is located externally to the air purifier.

17. The filter customization system of claim 1, wherein the first filter matrix comprises a first layer and a second layer.

* * * * *